(12) United States Patent
Haggard et al.

(10) Patent No.: US 6,753,007 B2
(45) Date of Patent: Jun. 22, 2004

(54) CONTROLLED RELEASE COMPOSITE

(75) Inventors: Warren Oliver Haggard, Bartlett, TN (US); Michael Earl Kaufman, Cordova, TN (US); Jack Eldon Parr, Memphis, TN (US); Linda Morris, Arlington, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 0 days.

(21) Appl. No.: 09/999,253

(22) Filed: Nov. 1, 2001

(65) Prior Publication Data

US 2002/0197315 A1 Dec. 26, 2002

Related U.S. Application Data

(63) Continuation of application No. 09/241,703, filed on Feb. 2, 1999, now abandoned.

(51) Int. Cl.⁷ ............................. A61F 13/00; A61K 9/14
(52) U.S. Cl. ........................................ 424/422; 424/489
(58) Field of Search ................................. 424/422, 426, 424/489, 423; 514/951

(56) References Cited

U.S. PATENT DOCUMENTS

| | | |
|---|---|---|
| 4,160,020 A | 7/1979 | Ayer et al. |
| 5,281,419 A | 1/1994 | Tuan et al. |
| 5,378,475 A | 1/1995 | Smith et al. |
| 5,512,055 A | 4/1996 | Domb et al. |
| 5,545,409 A | 8/1996 | Laurencin et al. |
| 5,607,474 A | 3/1997 | Athanasiou et al. |
| 5,614,206 A | 3/1997 | Randolph et al. |
| 5,629,009 A | 5/1997 | Laurencin et al. |
| 5,709,885 A | 1/1998 | Hellen et al. |
| 5,738,874 A | 4/1998 | Conte et al. |
| 5,756,127 A | 5/1998 | Grisoni et al. |
| 5,766,623 A | 6/1998 | Ayres et al. |
| 5,770,222 A | 6/1998 | Unger et al. |
| 5,773,019 A | 6/1998 | Ashton et al. |
| 5,780,055 A | 7/1998 | Habib et al. |
| 5,783,212 A | 7/1998 | Fassihi et al. |
| 5,807,567 A * | 9/1998 | Randolph et al. ........... 424/426 |
| 5,849,330 A | 12/1998 | Marvola et al. |

FOREIGN PATENT DOCUMENTS

| | | |
|---|---|---|
| DE | 196 20 117 C1 | 7/1997 |
| GB | 2 093 348 A | 9/1982 |
| WO | 98/36739 | 8/1998 |

* cited by examiner

*Primary Examiner*—Thurman K. Page
*Assistant Examiner*—S. Howard
(74) *Attorney, Agent, or Firm*—Fish & Richardson P.C.

(57) ABSTRACT

A composite is disclosed having a controlled rate of dissolution. The composite includes (a) a first region that includes a first composition that includes calcium sulfate, the first region exhibiting a first rate of dissolution; and (b) a second region that includes a second composition that includes calcium sulfate, the second region exhibiting a second rate of dissolution, the first rate of dissolution being different from the second rate of dissolution

13 Claims, No Drawings

CONTROLLED RELEASE COMPOSITE

This application is a continuation of pending U.S. Ser. No. 09/241,703, filed on Feb. 2, 1999 NOW ABANDONED.

BACKGROUND OF THE INVENTION

The invention relates to controllably dissolving a composite.

Controlled release of medication in vivo is the subject of much research. Various methods and release agents have been suggested, tested and marketed. Calcium sulfate has been utilized as filler for bone cavities as it is capable of being spontaneously adsorbed and replaced by bone. Calcium sulfate, formed from the hemihydrate, has been used as a controlled release agent alone for the filling of bone cavities and in combination with additives such as medicaments and pesticides. As a carrier for medicaments, it has been useful in vivo because it is biocompatible and is progressively resorbed by the body, thereby eliminating the need for secondary surgical procedures.

One application for a calcium sulfate controlled release agent is the local delivery of medicaments in vivo. The ideal characteristics of a local medicament delivery system are (1) biodegradability, (2) biocompatibility, (3) prolonged pharmaceutical release (e.g., over a period of at least 4 to 6 weeks), (4) reproducibility, (5) predictable pharmacokinetics, and (6) controllability.

One of the disadvantages to the use of calcium sulfate as a carrier is that, for some medicaments, the medicament is eluted from the calcium sulfate matrix at too rapid of a rate.

SUMMARY OF THE INVENTION

In general, the invention features a composite having a controlled rate of dissolution. The composite includes at least two regions, each of which includes a composition that includes calcium sulfate. A first region of the composite exhibits a rate of dissolution that is different from a second region of the composite. These composites are useful for filling bone voids and for delivering calcium and medicaments in vivo for sustained periods of time. In one embodiment, the regions are in the form of layers. In another embodiment, the first region surrounds the second region.

The preferred calcium sulfate is selected from the group consisting of alpha-calcium sulfate hemihydrate, beta-calcium sulfate hemihydrate, calcium sulfate dihydrate prepared from alpha-calcium sulfate hemihydrate, calcium sulfate dihydrate prepared from beta-calcium sulfate hemihydrate, and combinations thereof.

In one embodiment, the first composition further includes a medicament, preferably a medicament selected from the group consisting of tetracycline hydrochloride, vancomycin, tobramycin, gentamicin, cephalosporin, cis-platinum, ifosfamide, methotrexate, doxorubicin hydrochloride, transforming growth factor beta, bone morphogenic protein, demineralized bone matrix ("DBM"), basic fibroblast growth factor, platelet-derived growth factor, polypeptide growth factors, lidocaine hydrochloride, bipivacaine hydrochloride, ketorolac tromethamine, or a combination thereof. In another embodiment, the second composition also includes a medicament.

In one embodiment, the first composition includes calcium sulfate dihydrate prepared from alpha-calcium sulfate hemihydrate, and preferably, the second composition includes calcium sulfate dihydrate prepared from beta-calcium sulfate hemihydrate.

Preferred compositions are prepared by contacting with an aqueous liquid an alpha-calcium sulfate hemihydrate having a mean particle size of from about 12 $\mu$m to about 23.5 $\mu$m. In one embodiment, at least 80% of the alpha-calcium sulfate hemihydrate has a particle size of from about 12 $\mu$m to about 22 $\mu$m more preferably from about 16 $\mu$m to about 22 $\mu$m. In preferred composites, from about 0.1% to about 2.0% of the alpha-calcium sulfate hemihydrate has a particle size of less than about 2 $\mu$m. In one embodiment, the alpha-calcium sulfate hemihydrate has a density of from about 2.6 to about 2.9 g/cm$^3$. In other embodiments, the alpha-calcium sulfate hemihydrate has a purity greater than 98 wt. % calcium sulfate hemihydrate. The preferred range for the BET surface area of the alpha-calcium sulfate hemihydrate is from about 0.2 m$^2$/g to about 1.0 m$^2$/g.

Preferably the calcium sulfate is prepared from alpha-calcium sulfate hemihydrate having a purity greater than 98 weight % ("wt. %") calcium sulfate hemihydrate, a BET surface area in the range of from about 0.35 m$^2$/g to about 0.9 m$^2$/g, a density in the range of from about 2.73 to about 2.80 g/cm$^3$, and a mean particle size of about 16 $\mu$m to about 22 $\mu$m. Preferably from about 90 to about 95 wt. % of the alpha-calcium sulfate hemihydrate has a particle size distribution from about 1 $\mu$m to about 45 $\mu$m.

In one embodiment, the first composition is prepared by contacting with an aqueous liquid calcium sulfate consisting essentially of beta-calcium sulfate hemihydrate having a mean particle size in the range of from about 10 $\mu$m to about 15 $\mu$m. In other embodiments, the beta-calcium sulfate hemihydrate has a purity greater than 98 wt. % calcium sulfate hemihydrate. The beta-calcium hemihydrate can also have a BET surface area of from about 4.5 m$^2$/g to about 7.5 m$^2$/g, more preferably from about 5 m$^2$/g to about 6 m$^2$/g, and a density of from about 2.5 g/cm$^3$ to about 2.6 g/cm$^3$. In another embodiment, the first composition is prepared by contacting with an aqueous liquid calcium sulfate consisting essentially of beta-calcium sulfate hemihydrate having a purity greater than 98 wt. % calcium sulfate hemihydrate, a BET surface area in the range of from about 4.5 m$^2$/g to about 7.5 m$^2$/g, a density in the range of from about 2.5 g/cm$^3$ to about 2.6 g/cm$^3$, and a mean particle size in the range of from about 13 $\mu$m to about 14 $\mu$m.

In another aspect, the invention features a method of delivering medicament in vivo. The method includes implanting the above-described composite into a mammal.

The composite of the invention permits the controlled dissolution of regions that include a calcium sulfate composition, as well as the controlled release of additives such as, e.g., medicaments and pesticides.

Other features and advantages of the invention will be apparent form the following description of the preferred embodiments thereof, and from the claims.

DESCRIPTION OF THE PREFERRED EMBODIMENTS

The composite includes two regions that exhibit different rates of dissolution with respect to each other. The regions of the composite are macroscopic and can exist in a variety of forms in the composite such as, e.g., layers and geometrical shapes, e.g., spheres. The regions can be continuous or discontinuous, and one or more regions can exist within another region or regions.

The regions consist of compositions that include calcium sulfate and, optionally, an additive. Examples of sources of calcium sulfate suitable for use in preparing the compositions include alpha-calcium sulfate hemihydrate powder, beta-calcium sulfate hemihydrate powder, calcium sulfate dihydrate powder made from calcium sulfate hemihydrate powders including alpha-calcium sulfate hemihydrate and beta-calcium sulfate hemihydrate, and combinations thereof.

A preferred alpha-calcium sulfate hemihydrate powder has a purity greater than 98 wt. % calcium sulfate hemihydrate, a BET surface area of from about 0.2 $m^2/g$ to about 1.0 $m^2/g$ (preferably from about 0.35 $m^2/g$ to about 0.9 $m^2/g$, more preferably from about 0.35 $m^2/g$ to about 0.7 $m^2/g$), a density of about 2.6 $g/cm^3$ to about 2.9 $g/cm^3$ (more preferably from about 2.73 $g/cm^3$ to about 2.80 $g/cm^3$), and a mean particle size of from about 12 $\mu$m to about 23.5 $\mu$m. Preferably from about 0.1% to about 2.0% of the alpha-calcium sulfate hemihydrate has a particle size of less than about 2.0 $\mu$m. Preferably at least 80% of the alpha-calcium sulfate hemihydrate has a particle size of from about 12 $\mu$m to about 22 $\mu$m, more preferably from about 16 $\mu$m to about 22 $\mu$m.

A preferred beta-calcium sulfate hemihydrate powder has a purity greater than 98 wt. % calcium sulfate hemihydrate, a BET surface area of from about 4.5 $m^2/g$ to about 7.5 $m^2/g$ (more preferably from about 5 $m^2/g$ to about 6 $m^2/g$), a density of from about 2.5 $g/cm^3$ to about 2.6 $g/cm^3$, and a mean particle size of from about 10 $\mu$m to about 15 $\mu$m (more preferably from about 13 $\mu$m to about 14 $\mu$m).

The calcium sulfate composition of each region, the combination of regions, and the composite can be selected to achieve a desired rate of elution of one or more additives present in the composite, a desired rate of dissolution of the pellet including its regions, and combinations thereof. The composite can include regions of calcium sulfate prepared from a single form of calcium sulfate (e.g., alpha-calcium sulfate hemihydrate or beta-calcium sulfate hemihydrate powder), or multiple forms of calcium sulfate (e.g., a combination of one or more of alpha-calcium sulfate hemihydrate, beta-calcium sulfate hemihydrate, and the dihydrate prepared from alpha-calcium sulfate hemihydrate and beta-calcium sulfate hemihydrate). One example of a useful composite includes an interior region of calcium sulfate dihydrate prepared from beta-calcium sulfate hemihydrate, and an exterior region surrounding the interior region where the exterior region includes calcium sulfate dihydrate prepared from alpha-calcium sulfate hemihydrate. Another example of a useful composite includes an interior region that includes calcium sulfate dihydrate prepared from alpha-calcium sulfate hemihydrate, and an exterior region surrounding the interior region where the exterior region includes calcium sulfate dihydrate made from beta-calcium sulfate hemihydrate. Other examples of composites include one or more calcium sulfate dihydrate regions prepared from a combination of alpha and beta-calcium sulfate hemihydrate.

One example of a useful calcium sulfate composition that includes a mixture of beta-calcium sulfate hemihydrate powder and alpha-calcium sulfate hemihydrate powder, includes a weight ratio of beta-calcium sulfate hemihydrate powder to alpha-calcium sulfate hemihydrate powder of between 0 and about 3. Narrower ranges of this ratio, e.g., 0 to about 0.11, 0 to about 0.05, and 0 to about 0.02, are also contemplated. When used to carry growth factors, the weight ratio of the beta-calcium sulfate hemihydrate powder to the alpha-calcium sulfate hemihydrate powder may range up to about 3:1.

The composition, a region of the composite, or the composite, itself, can also include additives that are controllably released as the region dissolves. Examples of suitable additives include medicaments and pesticides. Examples of useful medicaments include antibiotics, chemotherapeutic agents, growth factors, and analgesics. Examples of useful antibiotics include tetracycline hydrochloride, vancomycin, cephalosporins, and aminoglycocides such as tobramycin and gentamicin. Examples of chemotherapeutic agents include cis-platinum, ifosfamide, methotrexate, and doxorubicin hydrochloride (Adriamycin®). Examples of growth factors include transforming growth factor beta (TGF-Beta), bone morphogenic protein ("BMP"), demineralized bone matrix ("DBM"), basic fibroblast growth factor, platelet-derived growth factor, and other polypeptide growth factors. Examples of analgesics include anesthetics such as lidocaine hydrochloride (Xylocaine®), bipivacaine hydrochloride (Marcaine®), and non-steroidal anti-inflammatory drugs such as ketorolac tromethamine (Toradol®).

The composite can include distinct regions each containing 0 to about 25 wt. % additive, preferably about 2 wt. % to about 10 wt. % additive, most preferably about 2 wt. % to about 5 wt. % additive.

One method of preparing a composite includes preparing two or more regions, and then combining, e.g., through pressure, adhesion or molding, two or more regions to form the composite, e.g., a pellet, a tablet or other geometric shape. The regions can be prepared by combining a source of calcium sulfate with an aqueous liquid to form a calcium sulfate composition, and then molding or applying pressure to the calcium sulfate composition to form the region.

The aqueous liquid can include salt, e.g., sodium chloride, i.e., it may be a saline solution. An alpha- or beta-calcium sulfate hemihydrate powder will convert to the dihydrate form upon contact with water or saline. The water to calcium sulfate weight ratio is preferably in the range of from about 0.22 to about 1, more preferably in the range of from about 0.27 to about 0.35 for alpha-calcium sulfate hemihydrate, and from about 0.65 to about 0.85 for beta-calcium sulfate hemihydrate powder. The consistency of a calcium sulfate powder (i.e., ml solution/grams calcium sulfate) is proportional to its surface area and is dependent upon the morphology of the crystal.

Additives can be incorporated into the composite using a variety of methods including, e.g., incorporating the additive into the calcium sulfate powder mixture (e.g., by mixing the additive with the calcium sulfate in powdered form prior to forming the calcium sulfate and aqueous liquid composition), addition of the additive to the calcium sulfate and aqueous liquid composition, and impregnating the formed region with an additive, e.g., by contacting the region with an additive in the form of a liquid or aerosol. Another useful method for incorporating an additive into the composite includes dissolving or suspending the additive into a solution and subsequently impregnating the additive into the calcium sulfate powder.

The composite can be formulated to provide a predetermined rate of dissolution or rate of release. Factors that influence the rate of dissolution or rate of release of the composite include, e.g., the composition of the composite, the composition of the regions, and the structure of the composite, e.g., the location of the regions within the composite. In addition, the form of calcium sulfate, the number of different forms of calcium sulfate, and the amount of each form of calcium sulfate present in the composition can be selected to provide a region having a desired rate of dissolution.

The composite, or a region of the composite, can be pre-formed for ease of use or custom formulated to meet a specific rate of dissolution, or rate of release or profile, e.g., a release rate or profile specified by a surgeon during the performance of an operation.

The invention will now be further described by way of the following example.

EXAMPLES

Dissolution Test Procedure

The dissolution rate of a pellet was determined by immersing the pellet in distilled water and periodically taking it out of the solution so that the pellet could be weighed. 100 ml of distilled water was placed in a polyethylene bottle. A pellet was immersed in the distilled water and the bottle was then placed in a water bath maintained at 37° C.

At 24 hour intervals (+/−1 hour) the pellet was removed from the bottle, weighed ("wet weight"), dried in an oven at 40° C. for 40 minutes, and weighed again ("dry weight"). The weight was recorded to the nearest milligram.

The polyethylene bottle was then refilled with 100 ml of fresh distilled water and the dried pellet was immersed in the distilled water. The bottles were again placed in the water bath maintained at a temperature of 37° C.

The above process was repeated for 8 days or until the pellet had completely dissolved. The average weight % ("wt. %") pellet remaining at each interval for each of the pellets tested was determined.

Elution Test Procedure

The elution rate of the medicament from a pellet was determined by weighing a pellet and then placing the pellet in a water-tight plastic container containing 20 ml of phosphate buffered saline (Dulbeccos Phosphate Buffered Saline, Sigma Chemical Co.). The container was then immersed in a water bath maintained at 37° C. for 24 hours. After 24 hours, a 2–4 ml sample of the eluant was removed and pipeted into a labeled cryogenic vial, which was then used to determine the concentration of tobramycin present in the sample as described below.

A metal mesh captured the pellet as the remaining solution was discarded. The container was then filled with 20 ml of fresh phosphate buffered saline solution, and the pellet was again immersed in the saline solution for another 24 hour period. After 24 hours a 2–4 ml sample was removed from the container and tested to determine the concentration of tobramycin present in the sample, as described below. This process was repeated for a total of seven days.

The concentration of tobramycin present in the 2–4 ml samples was measured using a TDX FLx automated fluorescence polarization analyzer (Abbott Laboratories). To obtain a reading, the sample was diluted to a concentration in the range of between 1–10 ug/ml and analyzed by TDX to determine the concentration, in ug/ml, of tobramycin in the sample. Dilutions varied from 1000 to 1×, from day 1 to day 7, respectively. The average tobramycin concentration, in ug/ml, of the pellets tested was determined for each interval.

Sample Preparation

Example 1

Dual βT/αT Pellets

Pellets containing an outer layer prepared from beta-calcium sulfate hemihydrate and tobramycin and an inner core prepared from alpha-calcium sulfate hemihydrate and tobramycin ("dual βT/αT pellets") were prepared as follows. 5 g beta-calcium sulfate hemihydrate (U.S. Gypsum) and 0.09 g stearic acid (J. T. Baker) were combined and mixed on a roll mixer for approximately 10 minutes. 0.29 g tobramycin sulfate (Eli Lilly) dissolved in 3.75 g water was combined with 5.09 g of the beta-calcium sulfate/stearic acid mixture. The composition was allowed to hydrate for 1 minute and then mixed for one minute to form a paste.

The resulting paste was cast into a bottomless mold. A 3 mm Osteoset T pellet prepared from alpha-calcium sulfate hemihydrate and 4% tobramycin sulfate (Eli Lilly) was inserted into the paste in the mold cavity. The paste was smoothed around the pellet to completely cover the pellet to form a dual βT/αT pellet. The dual βT/αT pellet was covered and allowed to dry for 15 minutes at ambient temperature, and then turned over and allowed to dry for 2 minutes at ambient temperature. The dual βT/αT pellet was covered and dried for approximately 2 hours. The dual βT/αT pellet was then removed from the mold, placed in an oven and dried for approximately 5 hours at 40° C.

Dual βT/αT pellets made by this process yielded, on average, 4% by weight tobramycin sulfate (approximately 3.2 mg/composite).

Example 2

Dual αT/βT Pellets

Pellets containing an outer layer prepared from alpha-calcium sulfate hemihydrate and tobramycin and an inner core prepared from beta-calcium sulfate hemihydrate and tobramycin ("dual αT/βT pellets") were prepared as follows. 20 g alpha-calcium sulfate hemihydrate (USG) was combined with 0.38 g stearic acid and mixed on a roll mixer for approximately 10 minutes. 1.14 g tobramycin sulfate dissolved in 5 g water was combined with 20.38 g of the alpha-calcium sulfate/stearic acid mixture. The composition was allowed to hydrate for 1 minute and then mixed for one minute to form a paste ("the alpha paste"). The resulting alpha paste was then cast into a bottomless 4.8 mm diameter mold.

A 3 mm calcium sulfate and tobramycin pellet prepared from beta-calcium sulfate hemihydrate ("the 3 mm beta pellet") was prepared as follows. 10 g beta-calcium sulfate hemihydrate and 0.18 g stearic acid were combined and mixed on a roll mixer for approximately 10 minutes. 0.58 g tobramycin sulfate dissolved in 7.5 g water was combined with 10.18 g of the calcium sulfate/stearic acid mixture. The composition was allowed to hydrate for 1 minute and then mixed for one minute to form a paste. The resulting paste was cast into a 3 mm diameter bottomless mold and dried to form a 3 mm beta pellet.

The dried 3 mm beta pellet was then inserted into the 4.8 mm mold cavity that had been filled with the above-described alpha paste. The alpha paste was smoothed over the surface of the beta pellet so as to encase the beta pellet and form a dual αT/βT pellet. The dual αT/βT pellet was cast at ambient temperature, turned over after 7 minutes, and allowed to dry for 5 minutes at ambient temperature. The dual αT/βT pellet was then covered and dried for approximately 2 hours. The dual αT/βT pellet was then removed from the mold, placed in an oven and dried for approximately 5 hours at 40° C.

Dual αT/βT pellets made by this process yielded 4% by weight tobramycin sulfate (approximately 4 mg/composite).

Example 3

Dual αT/αT Pellets

Pellets containing an outer layer prepared from alpha-calcium sulfate hemihydrate and tobramycin and an inner core prepared from alpha-calcium sulfate hemihydrate and tobramycin ("dual αT/αT pellets") were prepared and follows. 25 g alpha-calcium sulfate hemihydrate was combined with 0.475 g stearic acid and mixed on a roll mixer for approximately 10 minutes. 1.43 g tobramycin sulfate dissolved in 6.25 g water was combined with 24.475 g of the alpha-calcium sulfate/stearic acid mixture. The composition was allowed to hydrate for 1 minute and then mixed for one minute to form a paste. The resulting paste was cast into a bottomless mold.

A 3 mm Osteoset T pellet prepared from alpha-calcium sulfate hemihydrate and containing 4% tobramycin sulfate (Eli Lilly) was inserted into an empty mold and covered over with the above-described paste to form a dual αT/αT pellet. The dual αT/αT pellet was cast at ambient temperature, turned over after 10 minutes, and allowed to dry for 4 minutes at ambient temperature. The dual αT/αT pellet was covered and dried for approximately 48 hours. The dual αT/αT was then removed from the mold, placed in an oven and dried for approximately 8.5 hours at 40° C.

Dual αT/αT pellets made by this process yielded 4% by weight tobramycin sulfate (approximately 4.6 mg/composite).

Five pellets prepared according to each of Examples 1–3 were tested according to the Dissolution Test Procedure set forth above. The average wt. % of pellet remaining at each interval for Examples 1–3 is recorded in Table 1. Three pellets prepared according to each of Examples 1–3 were tested according to the Elution Test Procedure set forth above. The average tobramycin concentration in ug/ml of three pellets of each of Examples 1–3 is recorded in Table 2.

TABLE 1

| Example | Day 0 Ave. % residual | Day 1 Ave. % residual | Day 2 Ave. % residual | Day 3 Ave. % residual | Day 4 Ave. % residual | Day 5 Ave. % residual | Day 6 Ave. % residual | Day 7 Ave. % residual | Day 8 Ave. % residual |
|---|---|---|---|---|---|---|---|---|---|
| 1. Dual βT/αT | 100 | 62.4 | 38.8 | 22.2 | 10.0 | 3.0 | 0.0 | | |
| 2. Dual αT/βT | 100 | 67.8 | 39.1 | 23.6 | 9.1 | 1.6 | 0.0 | | |
| 3. Dual αT/αT | 100 | 71.3 | 50.4 | 33.0 | 19.6 | 9.8 | 3.8 | 0.5 | 0.0 |

TABLE 2

| Example | Ave. Initial wt of Composite (mg) | Ave Initial wt of tobramycin (mg) | Day 1 Ave. Concentration (ug/ml) | Day 2 Ave. Concentration (ug/ml) | Day 3 Ave Concentration (ug/ml) | Day 5 Ave Concentration (ug/ml) | Day 7 Ave Concentration (ug/ml) | Day 10 Ave Concentration (ug/ml) | Day 15 Ave Concentration (ug/ml) | Day 22 Ave Concentration (ug/ml) |
|---|---|---|---|---|---|---|---|---|---|---|
| 1. Dual βT/αT | 639.0 | 17.12 | 750 | 60.9 | 16.2 | 6.4 | 3.5 | 3.3 | 3.5 | 5.0 |
| 2. Dual αT/βT | 813.7 | 21.81 | 820 | 78.8 | 9.7 | 5.5 | 3.1 | | | |
| 3. Dual αT/αT | 956.3 | 25.41 | 1277 | 130.5 | 41.1 | 17.3 | 6.6 | 5.0 | 0.0 | |

Other embodiments are within the following claims. For example, although the composite has been described as having two regions, the composite can include multiple regions of different calcium sulfate compositions such that within one composite there exists multiple regions having differing dissolution rates. In addition, each region can include one or more additives.

What is claimed is:

1. A composite having a controlled rate of dissolution, said composite comprising:
   (a) a first region comprising a first composition that comprises calcium sulfate, said first region exhibiting a first rate of dissolution; and
   (b) a second region comprising a second composition that comprises calcium sulfate, said second region exhibiting a second rate of dissolution,
   said first rate of dissolution and said second rate of dissolution being different with respect to each other.

2. The composite of claim 1, wherein said calcium sulfate of said first composition is selected from the group consisting of alpha-calcium sulfate hemihydrate, beta-calcium sulfate hemihydrate, calcium sulfate dihydrate, or a combination thereof.

3. The composite of claim 2, wherein said calcium sulfate of said second composition is selected from the group consisting of alpha-calcium sulfate hemihydrate, beta-calcium sulfate hemihydrate, calcium sulfate dihydrate, or a combination thereof.

4. The composite of claim 1, wherein said regions are layers.

5. The composite of claim 1, wherein said first region surrounds said second region.

6. The composite of claim 1, wherein said first composition further comprises a medicament.

7. The composite of claim 6, wherein said second composition further comprises a medicament.

8. The composite of claim 6, wherein the medicament is selected from the group consisting of tetracycline hydrochloride, vancomycin, tobramycin, gentamicin, cephalosporin, cis-platinum, ifosfamide, methotrexate, doxorubicin hydrochloride, transforming growth factor beta, bone morphogenic protein, demineralized bone matrix, basic fibroblast growth factor, platelet-derived growth factor, polypeptide growth factors, lidocaine hydrochloride, bipivacaine hydrochloride, ketorolac tromethamine, or a combination thereof.

9. The composite of claim 7, wherein the medicament is selected from the group consisting of tetracycline hydrochloride, vancomycin, tobramycin, gentamicin, cephalosporin, cis-platinum, ifosfamide, methotrexate, doxorubicin hydrochloride, transforming growth factor beta, bone morphogenic protein, demineralized bone matrix, basic fibroblast growth factor, platelet-derived growth factor, polypeptide growth factors, lidocaine hydrochloride, bipivacaine hydrochloride, ketorolac tromethamine, or a combination thereof.

10. The composite of claim 1, wherein said first composition comprises calcium sulfate dihydrate prepared from alpha-calcium sulfate hemihydrate and said second composition comprises calcium sulfate dihydrate prepared from beta-calcium sulfate hemihydrate.

11. The composite of claim 1, wherein said calcium sulfate of the first composition consists essentially of alpha-calcium sulfate hemihydrate having a purity greater than 98 wt. % calcium sulfate hemihydrate, a BET surface area in the range of from about 0.35 m$^2$/g to about 0.9 m$^2$/g, a density in the range of from about 2.73 to about 2.80 g/cm$^3$, and a mean particle size of from about 16 µm to about 22 µm.

12. The composite of claim 1, wherein said calcium sulfate of the second composition consists essentially of beta-calcium sulfate hemihydrate having a purity greater than 98 wt. % calcium sulfate hemihydrate, a BET surface area in the range of from about 4.5 m$^2$/g to about 7.5 m$^2$/g, a density in the range of from about 2.5 to about 2.6 g/cm$^3$, and a mean particle size of about 13 µm to about 14 µm.

13. A method of delivering medicament in vivo comprising implanting a composite in a mammal, said composite comprising
   (a) a first region comprising a first composition that comprises calcium sulfate, said first region exhibiting a first rate of dissolution,
   (b) a second region comprising a second composition that comprises calcium sulfate, said second region exhibiting a second rate of dissolution,
   said first rate of dissolution and said second rate of dissolution being different with respect to each other, and
   (c) a medicament.

* * * * *